(12) United States Patent
Roe et al.

(10) Patent No.: US 12,036,399 B2
(45) Date of Patent: Jul. 16, 2024

(54) COIL SHUNTING FOR VOLTAGE LIMITING OF INDUCTIVELY TRANSFERRED POWER

(71) Applicant: Medtronic, Inc., Minneapolis, MN (US)

(72) Inventors: Jacob A. Roe, North St. Paul, MN (US); Joel B. Artmann, Elk River, MN (US); Jonathan P. Roberts, Coon Rapids, MN (US); David J. Peichel, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 975 days.

(21) Appl. No.: 17/021,180

(22) Filed: Sep. 15, 2020

(65) Prior Publication Data
US 2022/0080089 A1  Mar. 17, 2022

(51) Int. Cl.
*A61M 60/148* (2021.01)
*H01F 38/14* (2006.01)
*H02J 50/10* (2016.01)

(52) U.S. Cl.
CPC ........... *A61M 60/148* (2021.01); *H01F 38/14* (2013.01); *H02J 50/10* (2016.02)

(58) Field of Classification Search
CPC ... A61M 60/873; H01F 38/14; H02J 2310/23; H02J 50/10; H02J 50/80; H04B 5/0037; H04B 5/0075
See application file for complete search history.

(56) References Cited

U.S. PATENT DOCUMENTS

| | | |
|---|---|---|
| 4,216,756 A | 8/1980 | Mura |
| 4,665,896 A | 5/1987 | LaForge et al. |
| 6,442,434 B1 | 8/2002 | Zarinetchi et al. |
| 8,129,864 B2 | 3/2012 | Baarman et al. |
| 2002/0123779 A1 | 9/2002 | Zarinetchi et al. |
| 2012/0157753 A1 | 6/2012 | D'Ambrosio |
| 2016/0206799 A1* | 7/2016 | Lucke ............... A61N 1/37223 |
| 2018/0254631 A1 | 9/2018 | White, II et al. |

OTHER PUBLICATIONS

International Search Report and Written Opinion of International Application No. PCT/US2021/046446, mailed Dec. 7, 2021, 10 pp.

* cited by examiner

*Primary Examiner* — Scott Luan (74) *Attorney, Agent, or Firm* — Shumaker & Sieffert, P.A.

(57) ABSTRACT

An internal controller and an external power transmitter of an implanted medical device system and method therefore are provided. According to one aspect, an external power transmitter as part of a implanted medical device system includes processing circuitry configured to detect a shunting condition of an internal coil of the implanted medical device system, and responsive to detecting a shunting condition, reduce a magnitude of power transmitted to the internal coil.

22 Claims, 5 Drawing Sheets

FIG. 1

Prior Art

COIL SHUNTING FOR VOLTAGE LIMITING OF INDUCTIVELY TRANSFERRED POWER

CROSS-REFERENCE TO RELATED APPLICATION n/a

FIELD

The present technology is generally related to implantable medical devices such as a left ventricular assist device (LVAD), and more particularly to coil shunting for voltage limiting of inductively transferred power.

BACKGROUND

Figure 1:
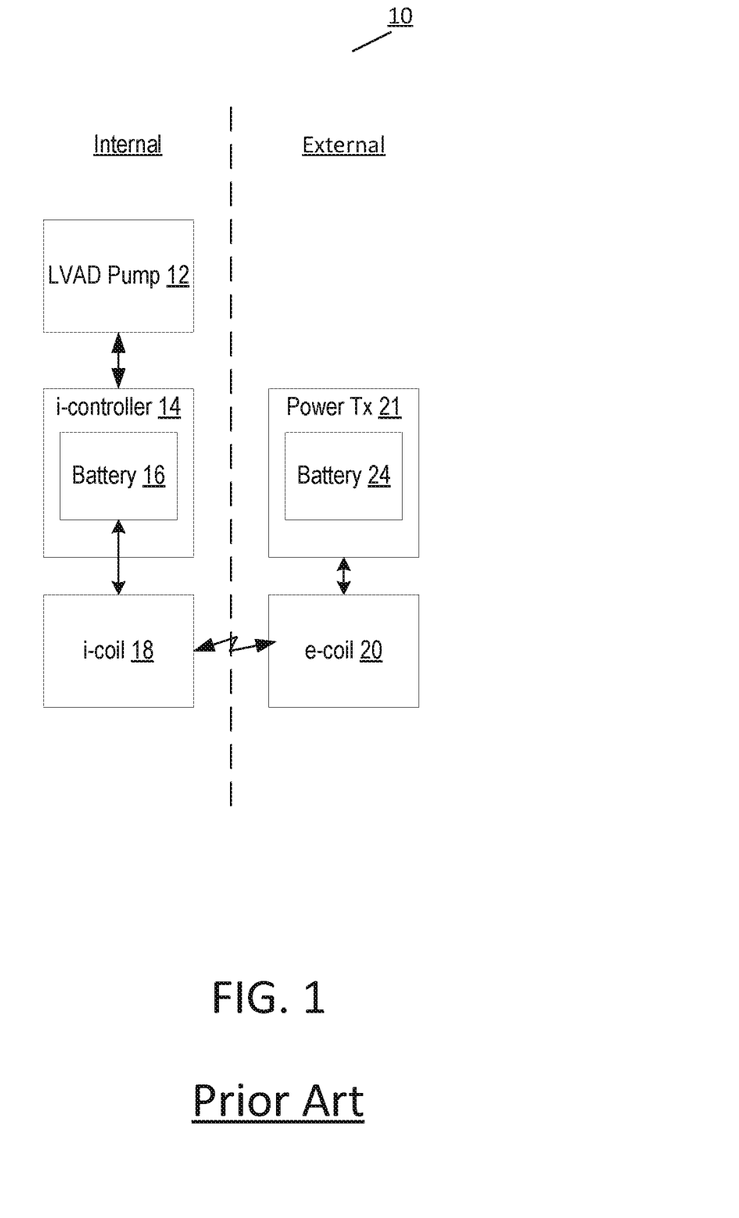
FIG. 1 is a block diagram of an implantable LVAD system.

Referring to FIG. 1, an implantable LVAD system 10 has internal components (in the body of the patient) and external components. The LVAD system 10 may typically include an LVAD pump 12 an implanted controller (i-controller) 14 having an internal battery 16, an implanted internal transcutaneous energy transfer system (TETS) coil (i-coil) 18, an external TETS coil (e-coil) 20 and an external power transmitter 21 with a detachable battery 24. In operation, power is supplied from the external power transmitter 21 to the i-controller 14 via mutual coupling of the coils 18 and 20, in order to charge the internal battery 16 of the i-controller 14 and to power the LVAD pump 12. The coils 18 and 20 transfer power by mutual induction of electromagnetic energy over the air and through the body. The power supplied by the external power transmitter 21 may come from the detachable battery 24 or from a wall outlet, for example.

SUMMARY

The techniques of this disclosure generally relate to coil shunting for voltage limiting of inductively transferred power.

According to one aspect, an internal controller implantable within a body of a patient as part of a implanted medical device system is provided. The internal controller includes processing circuitry configured to: detect an overvoltage condition of circuitry implanted in the patient; and shunt an internal coil in response to detecting the overvoltage condition.

According to this aspect, in some embodiments, the shunting is by shorting terminals of the internal coil. In some embodiments, the shunting is by connecting terminals of the internal coil to a common voltage. In some embodiments, the processing circuitry is further configured to receive power via discharge of a capacitance during the shunting. In some embodiments, the internal coil is shunted to increase a magnitude of a communication signal to be transmitted by the internal coil. In some embodiments, detecting an overvoltage condition includes comparing a fixed voltage level to a rectified and filtered voltage received by the internal coil.

According to another aspect, a method implemented in a controller implantable within a body of a patient as part of an implanted medical device system is provided. The method includes detecting an overvoltage condition of circuitry implanted in the patient and shunting an internal coil in response to detecting the overvoltage condition.

According to this aspect, in some embodiments, the shunting is by shorting terminals of the internal coil. In some embodiments, the shunting is by connecting terminals of the internal coil to a common voltage. In some embodiments, the method further includes receiving power via discharge of a capacitance during the shunting. In some embodiments, the method also includes shunting the internal coil to increase a magnitude of a communication signal to be transmitted by the internal coil. In some embodiments, detecting an overvoltage condition includes comparing a fixed voltage level to a rectified and filtered voltage received by the internal coil. In some embodiments, the method of detecting an overvoltage condition consists of comparing a fixed voltage level representative of overvoltage to a rectified and filtered voltage as received by the internal coil.

According to yet another aspect, an external power transmitter as part of an implanted medical device system is provided. The external power transmitter includes processing circuitry configured to: detect a shunting condition of an internal coil of the implanted medical device system; and responsive to detecting a shunting condition, reduce a magnitude of power transmitted to the internal coil.

According to this aspect, the processing circuitry is further configured to estimate a shunting duty cycle. In some embodiments, the estimate is used to determine an amount by which to reduce power transmitted to the internal coil. In some embodiments, the processing circuitry is further configured to determine an amount by which to reduce power transmitted to the internal coil based on a digitally encoded signal from an internal controller implanted within a patient. In some embodiments, the detecting includes determining a magnitude of current in an external coil coupled to the external power transmitter.

According to another aspect, a method in an external power transmitter of an implanted medical device system is provided. The method includes detecting a shunting condition of an internal coil of the implanted medical device system; and responsive to detecting a shunting condition, reducing a magnitude of power transmitted to the internal coil.

According to this aspect, in some embodiments, the method also includes estimating a shunting duty cycle. In some embodiments, the estimate is used to determine an amount by which to reduce power transmitted to the internal coil. In some embodiments, the method includes determining an amount by which to reduce power transmitted to the internal coil based on a digitally encoded shunting signal from an internal controller implanted within a patient. In some embodiments, the detecting includes determining a magnitude of current in an external coil coupled to the external power transmitter.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Some embodiments described herein are related to coil shunting for voltage limiting of inductively transferred power. Coil shunting refers to directing current from the internal coil thru a pathway other than to the load. The coil shunting may be achieved by shorting the terminals of the internal coil or by connecting the terminals to the same reference voltage. Coil shunting may be useful when communication with an external power transmitter is inhibited or prohibited, such as in the event of an internal component failure or in the event that the external power transmitter is incompatible with communication over the inductive power link. Coil shunting may also be useful to increase a magnitude of a communication signal to be transmitted to the external power transmitter under high power transfer scenarios.

Figure 2:
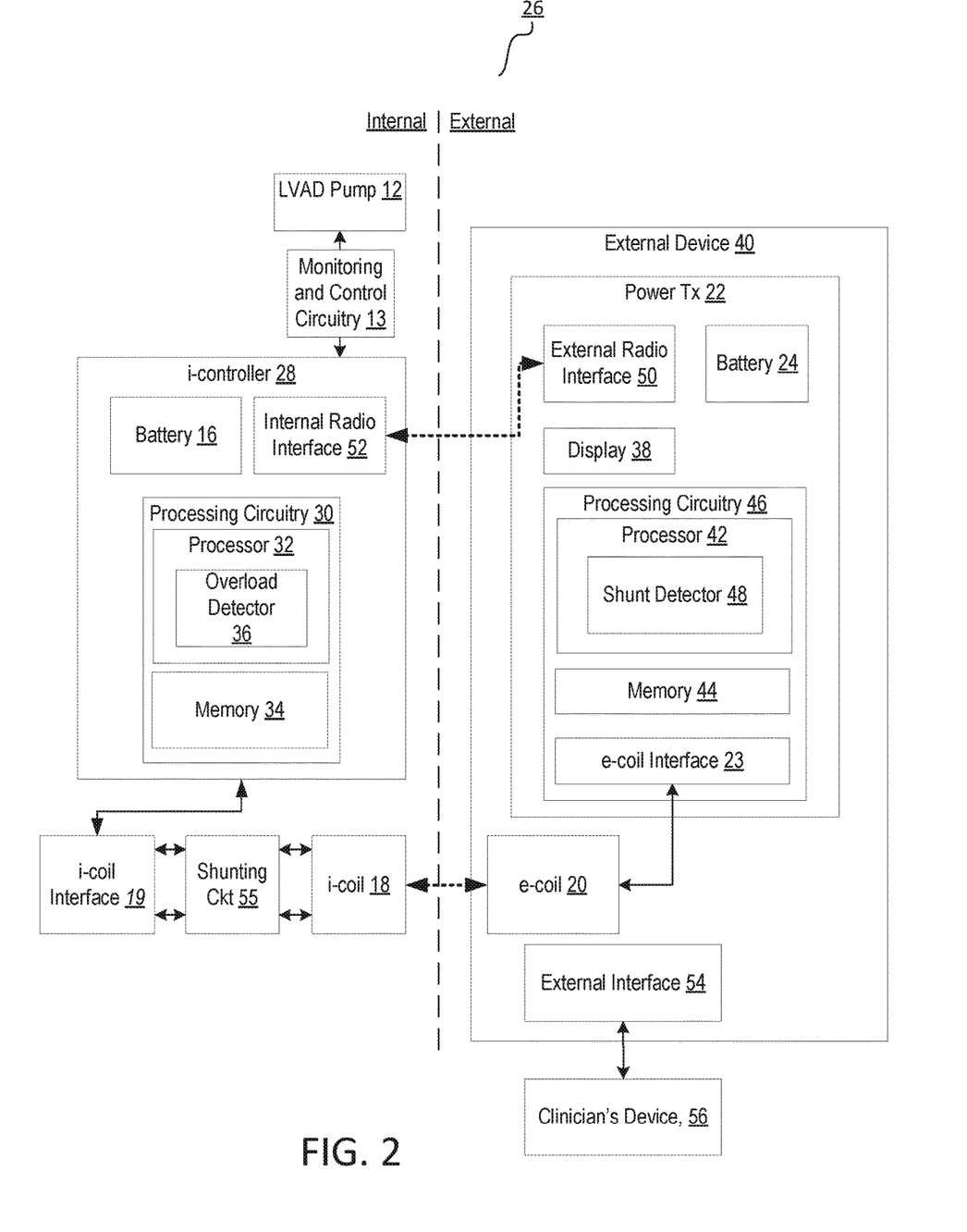
FIG. 2 is a block diagram of an embodiment of an LVAD system that implements a process of coil shunting for voltage limiting of inductively transferred power.

FIG. 2 shows a block diagram of one example configuration of an implanted medical device system 26 having external components such as an external power transmitter 22, and internal components such as an internal controller (i-controller) 28 configured to perform functions described herein. As used herein, the term "implanted medical device system 26" refers to the system that includes both the implanted/implantable components as well as external components described herein.

The i-controller 28 may have processing circuitry 30 which may include a processor 32 and an internal memory 34. The processor 32 may be configured to execute computer instructions stored in the internal memory 34. Those instructions may include instructions to cause the processor to perform some of the processes described in more detail below. The processor 32 may therefore implement an overload detector 36. The overload detector 36 detects when a component of the internal circuitry experiences a voltage overload. When the overload detector 36 detects a voltage overload, the processing circuitry 30 may cause a shunting circuit 55 to shunt the terminals of the i-coil 18 together or to a common potential so that the voltage applied to the i-coil interface 19 is zero.

A message or result from the internal controller 28 may be transferred from the i-controller 28 to an external display 38 of an external device 40, which may include a processor 42 and a memory 44 within processing circuitry 46, the external power transmitter 22 and the detachable battery 24, as well as the e-coil 20 in some embodiments. The memory 44 may be configured to store computer instructions to be executed by the processor 42 and may also be configured to store computer instructions for implementation of shunt detector 48. The shunt detector 48 is configured to detect when the i-coil 18 is shunted. The external display 38 may be configured to display information received from the i-controller 28.

Electrical communication of signals and power between the internal components of i-controller 28 may be via communication busses and individual electrical conductors not shown in FIG. 2. For example, a multi-conductor address bus and data bus may connect processor 32 with internal memory 34. In some embodiments, an i-coil interface 19 associated with i-coil 18 may be included in the set of internal components making up the implanted medical device system 26. One purpose of i-coil interface 19 may be to modulate the alternating current applied to the i-coil 18 with signals from the i-controller 28 to be transmitted from the i-coil 18 to the e-coil 20 and/or to demodulate signals to be received by the i-coil 18 from the e-coil 20. In some embodiments, a purpose of the i-coil interface 19 is to provide conversion between the alternating current (AC) of the i-coil 18 and direct current (DC) to charge the internal battery 16.

The power supplied to the i-coil 18 may be adjusted by varying the AC electrical current in the e-coil 20. Some or all functions of the i-coil interface 19 may be included in the i-controller 28 and/or the i-coil 18. In some embodiments, the i-coil 18 and/or i-coil interface 19 may be internal to or considered part of the internal controller 28. Similarly, electrical communication of signals and power between the internal components of external device may be by communication busses and individual electrical conductors not shown in FIG. 2. For example, a multi-conductor address bus and data bus may connect processor 42 with memory 44. In some embodiments, an e-coil interface 23 associated with e-coil 20 may be included in the set of external components making up the implanted medical device system 26. The e-coil interface 23 may include a TETS interface configured to demodulate information signals from the processing circuitry 30 transmitted from the i-coil 18 to the e-coil 20. The e-coil interface 23 may also be configured to couple power from the external power transmitter 22 to the e-coil 20. In some embodiments, the e-coil interface 23 may be two distinct units, one unit for demodulation of signals from the i-controller that are uploaded via the coils 18 and 20, and one unit for coupling power from the external power transmitter 22 to the e-coil 20. In some embodiments, the i-controller 28 may upload information to the external power transmitter 22 via the coils 18 and 20, but the power transmitter does not download information to the i-controller 28 via the coils 18 and 20.

In some embodiments, the internal components of the implanted medical device system 26 may include monitoring and control circuitry 13. A purpose of monitoring and control circuitry 13 may include monitoring speed and temperature, for example, of the LVAD pump 12. Another purpose of the monitoring and control circuitry 13 may include controlling the speed of the LVAD pump 12. Another purpose of the monitoring and control circuitry 13 may include monitoring the temperature of the i-controller 28, the i-coil 18 and/or the implanted battery 16. In some embodiments, some or all of the monitoring and control circuitry 13 may be incorporated into the LVAD pump 12 and/or the i-controller 28. In some embodiments, some or all of the functions performed by the monitoring and control circuitry 13 may be performed by the processing circuitry 30. Thus, in some embodiments, the monitoring and control circuitry 13 may include one or more temperature sensors embedded in the LVAD pump 12, the i-controller 28, the i-coil 18 and/or implanted battery 16. Information obtained from and/or about the LVAD pump 12, such as speed and temperature, may be sent to the external device 40 to be displayed by external display 38. Note that although an LVAD pump 12 is shown, other internal devices may be powered and controlled by the i-controller 28 instead of or in addition to an LVAD pump 12.

The various internal components making up the LVAD system may be grouped into one or more separate housings. Similarly, the various external components making up the LVAD system may be grouped into one or more separate housings. Further, some of the components shown and described as being internal to the i-controller 28 may be instead, external to i-controller 28 in some embodiments. Similarly, some of the components shown and described as being internal to the external device 40 may be instead, external to external device 40, in some embodiments. Note further that some of the functions performed by processor 32 may be performed instead by processor 42.

Note that transfer of information from the external device 40 to the internal memory 34, and vice versa, may be by wireless radio frequency (RF) transmission (over the air and through the body when the i-controller 28 is implanted). Accordingly, in some embodiments, the external device 40 includes an external radio interface 50 and the i-controller 28 includes an internal radio interface 52. In some embodiments, the external radio interface 50 and the internal radio interface 52 are RF transceivers having both an RF receiver for receiving information wirelessly and an RF transmitter for transmitting information wirelessly. Such RF transceivers may be Bluetooth and/or Wi-Fi compliant, for example. In some embodiments, the RF receiver and RF transmitter within the external device 40 or within the i-controller 28 are integrated into one unit, whereas in some embodiments, they could be physically separate units.

Also, information may be communicated to the i-controller 28 from the external power transmitter 22 via the coils 18 and 20, by modulating a parameter of power transmission, such as modulating the frequency of the transmitted power, or by modulating a parameter of the i-coil interface 19, for example, by modulating a tuning capacitance of the i-coil interface 19 or by modulating the load level of the i-controller and/or the i-coil interface 19.

The external device 40 could be a patient's external device that has an external interface 54 which provides an interface between the external device 40 and a clinician's device 56. The clinician's device might, for example, have a USB port and interface 54 might include a USB port, so that a USB cable may connect the two ports. The clinician's device 56 may read data from the external device 40 and write information and control signaling to the external device 40, in some embodiments. In the alternative to a wireline connection, the interface 54 could include or be a radio interface.

The shunting circuit 55 may operate in one of two states: a non-shunting state, in which the i-coil 18 is not shunted and power is delivered to the i-controller 28 and a shunting state in which the i-coil 18 is shunted and no power is delivered to the i-controller 28. Shunted means that the terminals of the i-coil 18 are shorted together or connected to a common reference voltage. The shunting may be triggered by a detection of an overload condition by the overload detector 36. An overload condition is one in which too high a voltage is applied from the i-coil 18 to the i-controller 28. The shunting of the i-coil 18 can be detected by the shunt detector 48 of the external power transmitter 22. Note that one way of detecting shunting of the i-coil 18 includes observing a loss of communication followed by repeated fast changes in current in the e-coil 20. In response to the detection of shunting, the external power transmitter 22 may reduce the magnitude of power transmitted to the i-coil 18. Further, the external power transmitter 22 may estimate the ratio of the time during which the i-coil is shunted to a total time between shunting events. The external power transmitter 22, via the processing circuitry 46, may use the estimate to determine an adjustment amount for reducing the transmitted power delivered to the i-coil 18 via the e-coil 20. The external power transmitter 22 may also be configured to detect and decode a digitally encoded signal from the i-controller 28 based upon shunting and uses the signal to determine the adjustment to the transmitted power level.

The external power transmitter 22 detects shunting based on the measured magnitude of current in the e-coil 20. When shunting occurs, the energy taken out of the system changes from being a combination of the losses in the coils plus power transmitted to the electronics and pump to being only the losses in the coils. This causes the energy stored in the system to increase, which causes an increase of the peak current in the coils and peak voltage on tuning capacitors of the i-coil interface 19.

The average duty cycle of shunting (the shunting duration divided by the time between shunt events) may match the excess power level. Alternatively, the average duty cycle of not shunting may match the utilized power level. During the time that shunting is occurring, no power is received by the implanted electronics thru the i-coil interface 19, so the system is running from stored energy on a capacitance at the output of the rectifier circuit and the voltage on the capacitor will drop. During the time that shunting is not occurring, all of the available power to be received is transferred either to the electronics or to the capacitance. The energy being stored on the capacitance will increase the voltage level. Shunting is determined by the voltage level on the output capacitor and the net energy transitioned out of and in-to the capacitor will be zero over one shunting cycle. This means that the total energy received during the period that shunting is not occurring is being utilized by the i-controller 28. If shunting is occurring for 25% of the shunting cycle, then there is 25% excess energy that is not being utilized and 75% of the energy is being utilized. This means that the desired transmit power level can be estimated to be 75% of the currently transmitted level.

Figure 3:
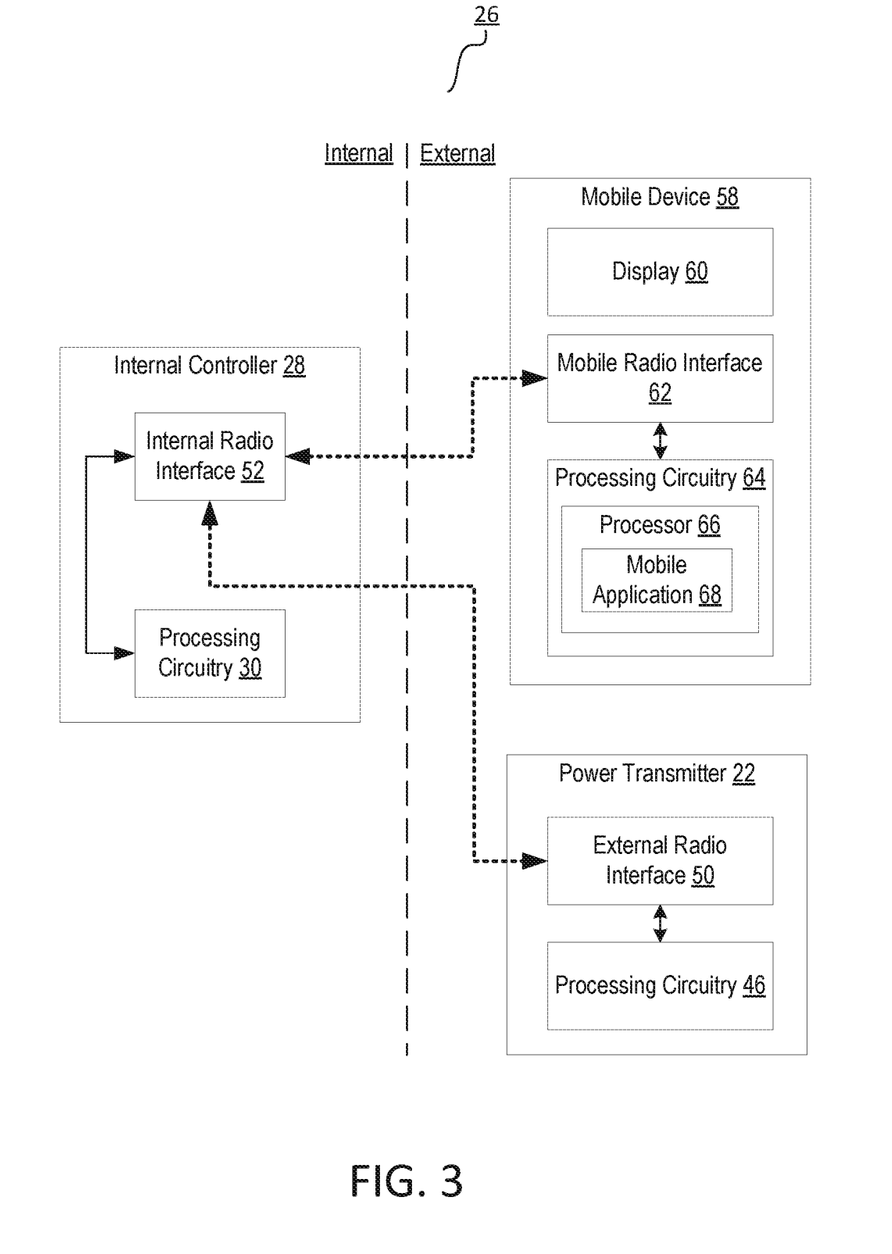
FIG. 3 is a block diagram of an implanted medical device system that includes a mobile device with a mobile application in wireless communication with an internal controller of the implanted medical device.

FIG. 3 is a block diagram of an implanted medical device system 26 that includes a mobile device 58 with a mobile application 68 in wireless communication with the i-controller 28. The mobile device 58 may be a mobile phone or other mobile digital device that can process information and communicate wirelessly with the i-controller. Accordingly, the mobile device 58 has a display 60, a mobile radio interface 62, processing circuitry 64, processor 66 which runs the mobile application 68. The radio interfaces 50, 52 and 62 may be Bluetooth Low Energy compatible radio interfaces, and the i-controller 28 may be a peripheral device responsible for advertising, while the mobile device 58 and the external power transmitter 22 may operate as master or central devices responsible for scanning and issuing connection requests.

Communication from the i-controller 28 to the external power transmitter 22 enables display on the external display 38 of implanted device information such as pump data and alarm indications. The i-controller 28 may exchange, via the radio interfaces 50 and 52, diagnostic and log file data with the external power transmitter 22. The i-controller 28 may receive programming commands from an external device such as the clinician's device 56 or mobile device 58. Further, communication from the i-controller 28 to the mobile device 58, via the radio interfaces 52 and 62, enables remote monitoring in cases where the mobile device 58 is connected to the Internet, and enables the display 60 to display information about the state of the implanted portion of the implanted medical device system 26 such as, for example, remaining battery runtime. In some embodiments, the internal radio interface 52 may only communicate with the external radio interface 50 and the mobile radio interface 62 one at a time. In some embodiments, when the i-controller 28 is not engaged in a communication session with an external device, such as external power transmitter 22 or mobile device 58, the i-controller 28 may advertise continually to enable rapid reestablishment of the wireless connection between the i-controller 28 and the external power transmitter 22 or mobile device 58. Conversely, either one or both of the external power transmitter 22 or mobile device 58 may scan for such advertisements.

Figure 4:
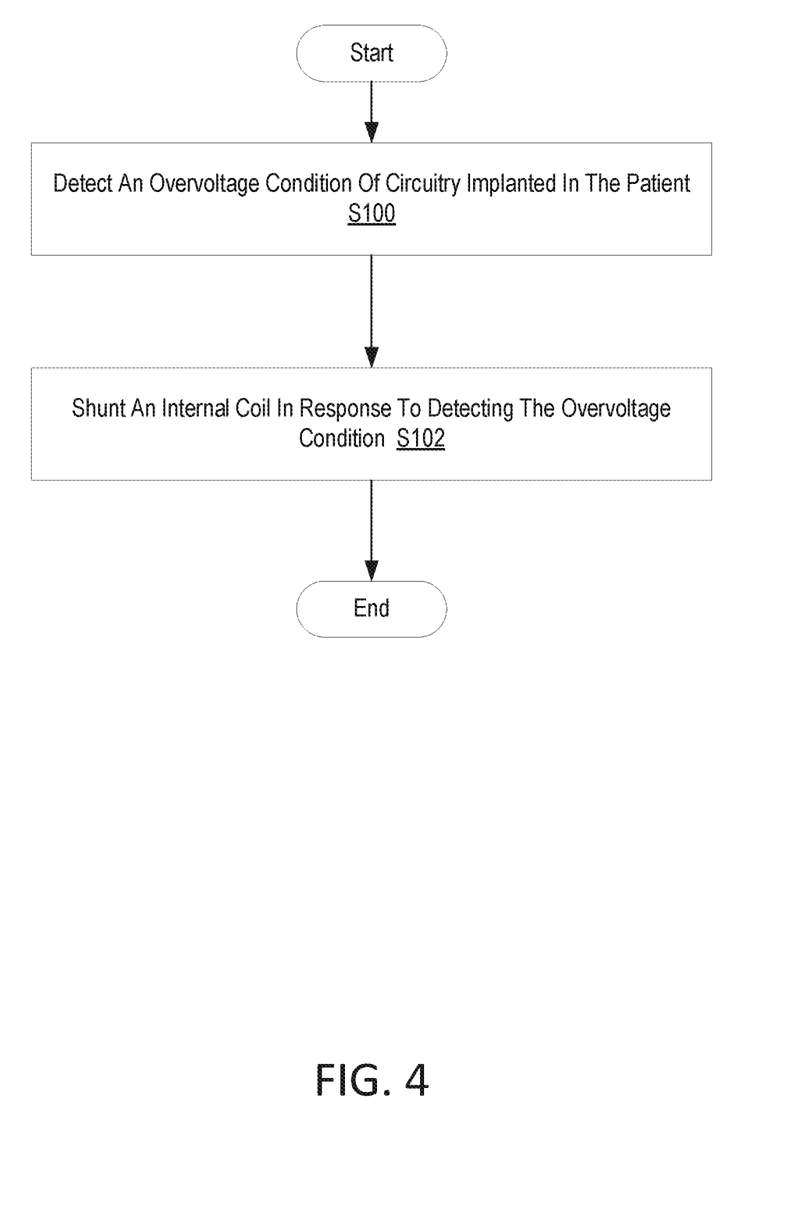
FIG. 4 is a flowchart of a process implemented in an internal device of an implanted medical device according to principles set forth herein.

FIG. 4 is a flowchart of an exemplary process implemented in an internal device of an implantable medical device for coil shunting for voltage limiting of inductively transferred power. The process includes detecting, via the overload detector 36, an overvoltage condition of circuitry implanted in the patient (Block S100). The process also includes shunting an internal coil in response to detecting the overvoltage condition (Block S102). The shunting is controlled by the i-controller 28.

Figure 5:
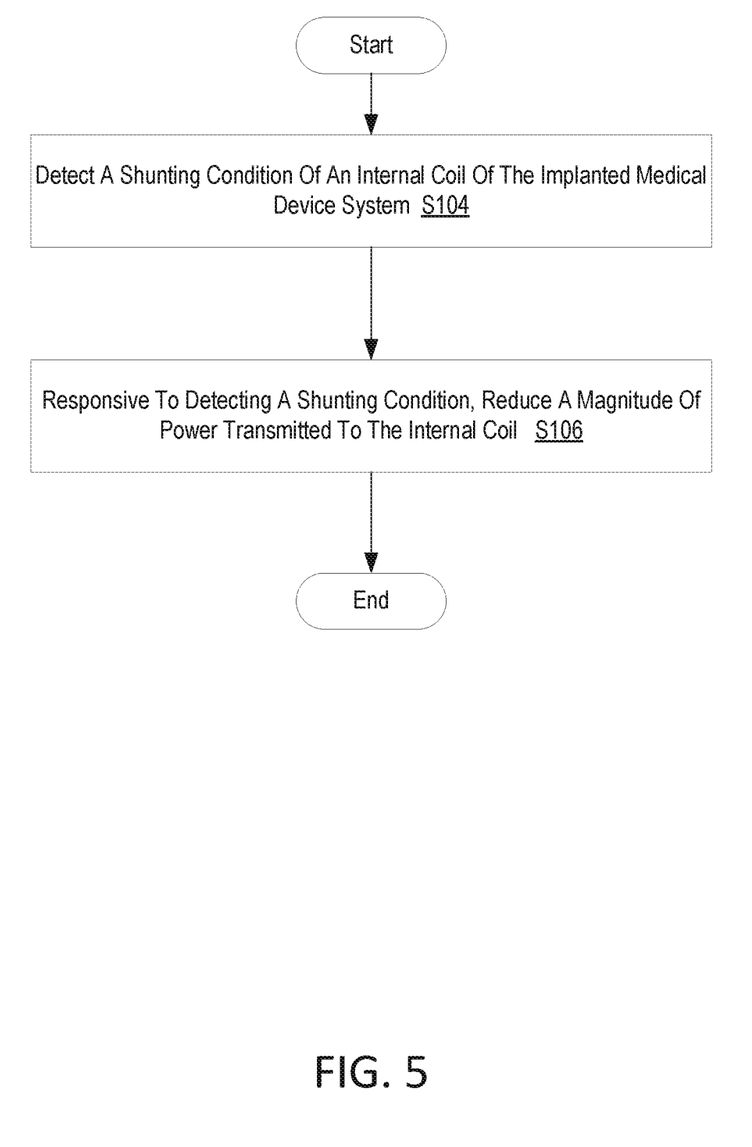
FIG. 5 is a flowchart of a process implemented in an external device of an implanted medical device according to principles set forth herein.

FIG. 5 is a flowchart of a process implemented in an external power transmitter of an implantable medical device for detecting and responding to a shunted coil condition. The process includes detecting, via the shunt detector 48, a shunting condition of an internal coil of the implanted medical device system (Block S104). The process also includes, responsive to detecting a shunting condition, reducing via the processing circuitry 46, a magnitude of power transmitted to the internal coil (Block S106).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media and memory may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An internal controller implantable within a body of a patient as part of a implanted medical device system, the internal controller comprising:
   a battery;
   an internal radio interface;
   an internal coil configured to inductively receive, from an external coil of an external device, power to charge the battery; and
   processing circuitry configured to:
      detect an overvoltage condition of circuitry implanted in the patient; and
      shunt the internal coil in response to detecting the overvoltage condition;
      cause the internal radio interface to transmit to the external device a digitally encoded signal for causing the external device to reduce a magnitude of power transmitted to the internal coil.

2. The internal controller of claim 1, wherein to shunt the internal coil, the processing circuitry is configured to short terminals of the internal coil.

3. The internal controller of claim 1, wherein to shunt the internal coil, the processing circuitry is configured to connect terminals of the internal coil to a common voltage.

4. The internal controller of claim 1, wherein the processing circuitry is further configured to receive power via discharge of a capacitance during the shunting.

5. The internal controller of claim 4, wherein shunting the internal coil causes an increase in a magnitude of a communication signal to be transmitted by the internal coil.

6. The internal controller of claim 1, wherein to detect the overvoltage condition, the processing circuitry is configured to compare a fixed voltage level to a rectified and filtered voltage received by the internal coil.

7. A method implemented in an internal controller implantable within a body of a patient as part of an implanted medical device system, the method including:
   detecting an overvoltage condition of circuitry implanted in the patient;
   shunting an internal coil in response to detecting the overvoltage condition, the internal coil being configured to inductively receive, from an external coil of an external device, power to charge a battery; and
   causing an internal radio interface to transmit to the external device a digitally encoded signal for causing the external device to reduce a magnitude of power transmitted to the internal coil.

8. The method of claim 7, wherein the shunting comprises shorting terminals of the internal coil.

9. The method of claim 7, wherein the shunting comprises connecting terminals of the internal coil to a common voltage.

10. The method of claim 7, further comprising receiving power via discharge of a capacitance during the shunting.

11. The method of claim 7, further comprising shunting the internal coil to increase a magnitude of a communication signal to be transmitted by the internal coil.

12. The method of claim 7, wherein detecting an overvoltage condition includes comparing a fixed voltage level to a rectified and filtered voltage received by the internal coil.

13. An external power transmitter as part of an implanted medical device system, the external power transmitter comprising:
- an external coil configured to transmit power to an internal coil of an implanted medical device of the medical device system;
- an external radio interface configured to communicate with the implanted medical device; and
- processing circuitry configured to:
  - detect a shunting condition of the internal coil of the implanted medical device based on detecting a loss of communication by the external radio interface with the implanted medical device and based on changes in current in the external coil; and
  - responsive to detecting a shunting condition, reduce a magnitude of power transmitted to the internal coil.

14. The external power transmitter of claim 13, wherein the processing circuitry is further configured to estimate a shunting duty cycle.

15. The external power transmitter of claim 14, determining an amount by which to reduce power transmitted to the internal coil based on the estimate.

16. The external power transmitter of claim 13, wherein the processing circuitry is further configured to determine an amount by which to reduce power transmitted to the internal coil based on a digitally encoded shunting signal from an internal controller implanted within a patient.

17. The external power transmitter of claim 13, wherein to detect the shunting condition, the processing circuitry is configured to determine a magnitude of current in an external coil coupled to the external power transmitter.

18. A method in an external power transmitter of an implanted medical device system, the method comprising:
- detecting a shunting condition of an internal coil of the implanted medical device system based on detecting a loss of communication by an external radio interface with an implanted medical device of the medical device system and based on changes in current in an external coil of the implanted medical device; and
- responsive to detecting a shunting condition, reducing a magnitude of power transmitted to the internal coil.

19. The method of claim 18, further comprising estimating a shunting duty cycle.

20. The method of claim 19, further comprising determining an amount by which to reduce power transmitted to the internal coil based on the estimate.

21. The method of claim 18, further comprising determining an amount by which to reduce power transmitted to the internal coil based on a digitally encoded signal from an internal controller implanted within a patient.

22. The method of claim 18, wherein detecting the shunting includes determining a magnitude of current in an external coil coupled to the external power transmitter.

* * * * *